United States Patent [19]

Takruri et al.

[11] 4,210,633
[45] Jul. 1, 1980

[54] FLURANDRENOLIDE FILM FORMULATION

[75] Inventors: Harun Takruri; Jane E. Chavers, both of Indianapolis, Ind.

[73] Assignee: Eli Lilly and Company, Indianapolis, Minn.

[21] Appl. No.: 953,160

[22] Filed: Oct. 20, 1978

[51] Int. Cl.² .................... A61K 31/79; A61K 31/58
[52] U.S. Cl. ...................... 424/80; 424/28; 424/241
[58] Field of Search ................ 424/80, 28, 241

[56] References Cited

U.S. PATENT DOCUMENTS

| | | | |
|---|---|---|---|
| 2,693,438 | 11/1954 | Ward | 424/28 |
| 2,861,920 | 11/1958 | Dale | 424/80 |
| 3,046,196 | 7/1962 | de Vaulchier | 424/28 |
| 3,214,338 | 10/1965 | Ehrlich | 424/28 X |
| 3,287,222 | 11/1966 | Larde et al. | 424/80 X |
| 3,551,556 | 12/1970 | Kliment et al. | 424/28 X |
| 3,598,123 | 8/1971 | Zaffaroni | 424/28 X |
| 3,608,070 | 9/1971 | Nouvel | 424/80 |
| 3,777,016 | 12/1973 | Gilbert | 424/80 |
| 4,120,949 | 10/1978 | Bapatla et al. | 424/80 |

FOREIGN PATENT DOCUMENTS

| | | | |
|---|---|---|---|
| 2224140 | 4/1973 | France | 424/80 |
| 564569 | 3/1968 | Switzerland . | |

*Primary Examiner*—Leonard Schenkman
*Attorney, Agent, or Firm*—James L. Rowe; Arthur R. Whale

[57] ABSTRACT

Film-forming formulation containing fluroandrenolide. The film can be removed by peeling or washing.

2 Claims, No Drawings

FLURANDRENOLIDE FILM FORMULATION

BACKGROUND OF THE INVENTION

There are several examples in the scientific and patent literature of medicaments being applied topically with the use of a bandage or continuous film. In the simplest instance, a continuous film is used as an occlusive dressing to prevent access of air to the treated area. In such a use, the medicament is first applied as a salve, cream or lotion to the affected skin area and the film is taped over the area at all film edges, but only at the edges. The presence of the film may also inhibit the evaporation of the medicament. Next, medicated gauze-like bandages have been used. U.S. Pat. No. 3,328,259 covers a wound dressing containing a hemostatic agent. The wound dressing itself is said to adhere to the skin through the inherent solubility of the film which will eventually be completely absorbed by the body. U.S. Pat. Nos. 2,772,999 and 2,773,000 disclose gauze bandages in which the gauze is impregnated with a hemostatic agent such as carboxymethyl cellulose. U.S. Pat. No. 3,287,222 discloses a wound dressing, preferably a vinyl chloride-vinylidine chloride polymer or a polyethylene glycol terephthalate or polyvinyl chloride polymer which may also contain medicinal agents. U.S. Pat. No. 2,624,690 also covers a medicated bandage. U.S. Pat. No. 3,579,628 relates to a wound dressing preparation comprising a hydrophilic acrylic film which may contain substances which react with water to generate a bacteriostat. The film may be bonded to a flexible carrier sheet which is separated after application to the wound. In none of the above does the medicated bandage adhere to the body surface--the wound itself-- by use of an adhesive, but the bandage is held in place at its edges with tape.

In other medicated bandages, the film itself is held on the skin area by an adhesive layer uniformly dispersed over the film surface. For example, U.S. Pat. No. 3,632,740 discloses an adhesive tape in which the adhesive can be a rubber-based polyvinyl alkyl ether and acrylate and the medicament dispersed therein is a corticosteroid.

U.S. Pat. No. 1,533,272 discloses an old-fashioned adhesive tape in which the adhesive is a rubbery material or a sticky gum but which may contain medicinal elements.

U.S. Pat. No. 3,598,123 discloses a bandage useful for the continuous administration of drugs. The bandage is a standard adhesive tape containing a plurality of microcapsules distributed throughout the adhesive, each of which contain a drug. An acrylic acid-acrylate copolymer is disclosed as the adhesive and the backing sheet is cellophane.

Swiss Pat. No. 564,569 claims a medicated adhesive tape adapted for direct application to a skin lesion comprising a nonporous flexible backing and a pressure-sensitive adhesive coating, preferably an acrylate ester-acrylic acid copolymer containing flurandrenolone acetonide (flurandrenolide) dispersed therein. Such a medicated adhesive tape is marketed in the United States as CORDRAN ® Tape by Eli Lilly and Company, Indianapolis, Indiana. U.S. Pat. No. Re. 24,906 covers the pressure-sensitive adhesive tape comprising a backing and an adhesive containing an acrylate ester copolymer used in the above medicament. Finally, U.S. Pat. No. 2,855,925 discloses an adhesive tape in which the pressure-sensitive adhesive may contain fungicides, bacteriocides, etc.—see also U.S. Pat. No. 3,267,871. The medicated film may also be formed in situ. For example, U.S. Pat. No. 2,973,300 describes a preparation for the treatment of topical ulcer comprising antibiotics, enzymes for debridement of the ulcer and a film-forming agent preferably polyvinylpyrrolidone as a carrier. The medicament is applied to the ulcerated area as a powder from which the film forms. U.S. Pat. No. 3,627,871 covers a therapeutic film-forming composition containing medicaments, particularly an anti-inflammatory steriod, and as the film-forming composition, an emulsion of a polyvinylidene chloride. The film must be capable of releasing the medicament to the underlying skin and be substantially water-vapor impermeable. Other polymeric film-forming agents disclosed include polyvinyl chloride, polystyrene, acrylic acid polymers and butadiene polymers. U.S. Pat., No. 3,821,363 discloses a sunscreen preparation comprising a gel of the acid form of a cross-linked copolymer of ethylenemaleic anhydride containing also a sunscreen agent. The preparation forms a film on the skin after evaporation of the water-carrier. U.S. Pat. No. 3,577,516 discloses a spray-on bandage comprising a hydrophilic water-insoluble hydroxy or lower alkoxy, lower alkyl acrylate or methacrylate polymer or copolymer containing a high boiling liquid plasticizer and various medicaments including germicides, fungicides, antibiotics, local anaesthetics, or anti-inflammatory steroids. The film is sprayed on as an aerosol in a preferred embodiment. U.S. Pat. No. 3,749,772 describes a film-forming acrylic polymer for use on the skin to prevent contact with poison ivy, the polymer also containing an oxidizing agent to break down the allergens in the poison ivy. U.S. Pat. No. 3,100,180 discloses a dermal protective composition which is to be applied in the form of a lotion. The lotion contains a latex-like dispersion of elastomeric vinyl polymer containing fluorine.

Other similar preparations include the following:
U.S. Pat. No. 2,693,438 deals with a pre-formed non-adherent film for application to open lesions. Polyvinyl alcohol is the film-forming composition of choice.

U.S. Pat. No. 2,804,073 discloses a fluid surgical dressing which can be administered from an aerosal-type container and in which the resin is a vinyl chloride vinyl acetate copolymer an n-butyl methylacrylate polymer, etc.

U.S. Pat. No. 3,269,903 covers a liquid plastic dressing which has the property of absorbing ultraviolet light; a number of such dressings are disclosed including such film-forming agents, as polymethylmethacrylate, polyisoamylmethacrylate, etc. After spraying, a film is formed by evaporation.

In addition, there are presently marketed non-medicated cosmetic masks which remove dirt, impurities and dead skin. The "mask" is brushed on in a solvent and dries to a continuous film which is removed customarily after 15 minutes. Such masks are invariably removed by peeling. A non-medicated skin mask which would adhere without cracking for 24 hours might also remove live skin as well as debris upon peeling. This property would not be desirable in a medicated mask used for treatment of skin lesions since the irritation and erythema produced on peeling could well be worse than the initial lesion, and at the least might exacerbate the condition.

None of the peelable films disclosed in the above references are capable of maintaining their integrity, and thereby excluding air from the treated skin surface, for the period of time required for heeling of the skin disease as is possible with ordinary occlusive dressings and with medicated adhesive tapes or bandages. Removal of medicated films or face masks by means other than peeling is not recorded.

It is an object of this invention to provide a film containing an anti-inflammatory steroid, such as flurandrenolide, as a medicament, which film avoids the disadvantages of films available from the prior art.

SUMMARY OF THE INVENTION

In fulfillment of the above and other objects, this invention provides a formulation capable of providing a medicated film of excellent lasting quality and adherence which can be removed after absorption of the medication either by peeling or washing with water. Such formulation contains the following ingredients:

| Ingredient | Preferred Embodiment, Weight in grams/100 g. of Formulation | Range Percent (w/w) |
| --- | --- | --- |
| Flurandrenolide | 0.1 | 0.01–0.5 |
| Polyvinyl Alcohol | 9.0 | 4–15 |
| Polyvinylpyrrolidone | 11.0 | 5–20 |
| Glycerin | 9.0 | 0–20 |
| Ethyl Alcohol | 10.0 | 0–30 |
| Benzyl Alcohol | 2.0 | 0–5 |
| Propylene Glycol | 3.0 | 0–20 |
| Disodium Edetate* | 0.02 | 0–0.5 |
| Citric Acid | 0.1 | 0–1 |
| Water q.s. to | 100.0 | |

*Ethylenediaminetetracetic acid, disodium salt.

The film-forming formulation is prepared by dissolving the anti-inflammatory corticosteroid, specifically flurandrenolide, in a suitable solvent such as propylene glycol, glycerine, ethyl alcohol, or mixtures thereof, and this solution is added to a mixture of the other ingredients including some water. After thorough mixing, sufficient water is added to make a quantity of formulation containing the above percentages of ingredients.

The above formulation is spread manually or with an applicator. Upon evaporation of the solvents including water over a period of from 20–30 minutes, a continuous medicated adherent film of from about 0.05–0.15 mm (average 0.08 mm) thickness is formed. After 18–24 hours, or other desirable time span, the film is removed with water or peeled.

Our novel medicated film has an additional property of slowly losing its adherance. This property manifests itself after 18–24 hours in situ where the film can be removed by peeling without harm to the underlying skin area. If it is necessary to remove the film sooner, as for example at 4 hours, when adherance is still strong, then water removal should be employed to avoid discomfort after peeling.

Other topically effective anti-inflammatory steroids which can be employed in preparing the medicated film of this invention include the 16-methyl steroids, such as flumethasone (6α,9α-difluoro-16α-methyl-1,4-pregnadiene-11β,17α,21-triol-3,20-dione), β-methasone (9α-fluoro-16β-methyl-1,4-pregnadiene-11β,17α,21-triol-3,20-dione), dexamethasone (9α-fluoro-16α-methyl-1,4-pregnadiene-11β,17α,21-triol-3,20-dione), and their 17α esters, particularly the valerate and caprate esters; other acetonides including triamcionolone 9α-fluoro-16α-hydroxycortisone-16α,17α-acetonide), 9α,11β-dichloro-6α-fluoro-1,4-pregnadiene-16α,17α,21-triol-3,20-dione-16α,17α-acetonide, 9α,11β-dichloro-6α,21-difluoro-1,4-pregnadiene-16α,17α-diol-3,20-dione-16α,17α-acetonide, 9α,11β-dichloro-6α-fluoro-1,4,6-pregnatriene-16α,17α,21-triol-3,20-dione-16α,17α-acetonide; and the standard cortiocosteroids, cortisone, hydrocortisone, prednisolone, medrol (6α-methylprednisolone) and the like. Also useful are the 21 esters of any of the above anti-inflammatory steroids, including the propionates, acetates, phosphates, pivalates, etc., thereof. These steroids are included at a concentration equivalent in anti-inflammatory activity to 0.01–0.5% by weight of flurandrenolide per 100 grams of formulation.

The medicated, water-soluble films of this invention are useful in treating persistent dermatoses, for example psoriasis, atopic, eczematous and neurodermatoses, which are responsive to treatment with an anti-inflammatory steroid. A person suffering from one of these persistent dermatoses and in need of treatment applies a formulation containing 0.01–0.5 percent by weight of flurandrenolide or a therapeutically-equivalent percent by weight of another topically-effective anti-inflammatory steroid to the skin lesion and allows the formulation to dry to a continuous film. After 18–24 hours, after which time the anti-inflammatory steroid has been substantially all transferred to the skin surface and absorbed, the film is removed with water or peeled. If medically necessary, the treatment can be repeated until a complete or partial cure is effected. The film thus formed maintains its integrity without peeling or cracking for periods of from 18–24 hours or longer. The film is thus a superior type of occlusive dressing and has low dermal toxicity. It is virtually non-irritating when applied, even without its content of anti-inflammatory steroid. Finally, the film, as long as it is in place, releases the steroid medicament continuously although in decreasing amounts. Clinical improvement with the film thus used is comparable to that seen with creams, lotions, etc. of similar steroid content.

Our novel film, as set forth above, can be removed by peeling or washing. It is an advantage of our medicated film that its adherance to the skin decreases with time, such that it can ordinarily be removed by peeling after, for example, 24 hours without irritating the underlying skin. However, our medicated film can also be removed by washing with water, a distinct advantage for persons with extremely sensitive skin or where it is desirable to remove the film after only a few hours, when adherance of the film is still good and peeling of the film might cause discomfort, erythema etc.

We claim:

1. The process of treating a lesion of a persistent dermatosis treatable by an anti-inflammatory steroid which comprises applying to a skin area of a human in which there is such a lesion, a formulation capable of forming a medicated water-soluble, adherent film containing the following ingredients in the percentages (w/w) given:

| Ingredient | Percent |
| --- | --- |
| Flurandrenolide | 0.01–0.5 |
| Polyvinyl Alcohol | 4–15 |
| Polyvinylpyrrolidone | 5–20 |
| Glycerin | 0–20 |
| Ethyl Alcohol | 0–30 |
| Propylene Glycol | 0–20 |
| Benzyl Alcohol | 0–5 |

| Ingredient | Percent |
| --- | --- |
| Disodium Edetate | 0–0.5 |
| Citric Acid | 0–1 |
| Water | q.s. to 100 | allowing the volatile constituents of the formulation to evaporate leaving a continuous adherent medicated film covering the lesion, and removing the film by peeling or with water after a period of at least 16 hours.

2. The process of treating a lesion of a persistent dermatosis treatable by an anti-inflammatory steroid which comprises applying to a skin area of a human in which there is such a lesion, a formulation capable of forming a medicated water-soluble, adherent film containing the following ingredients in the percentages (w/w) given:

| Ingredient | Weight in Grams/100 g. of Formulation |
| --- | --- |
| Flurandrenolide | 0.1 |
| Polyvinyl Alcohol | 9.0 |
| Polyvinylpyrrolidone | 11.0 |
| Glycerin | 9.0 |
| Ethyl Alcohol | 10.0 |
| Benzyl Alcohol | 2.0 |
| Propylene Glycol | 3.0 |
| Disodium Edetate | 0.02 |
| Citric Acid | 0.0 |
| Water q.s. to | 100.0 | allowing the volatile constituents of the formulation to evaporate leaving a continuous adherent medicated film covering the lesion, and removing the film by peeling or with water after a period of at least 16 hours.

* * * * *